United States Patent [19]

Hakky et al.

[11] Patent Number: 5,637,091
[45] Date of Patent: Jun. 10, 1997

[54] COLLAPSIBLE CATHETER

[76] Inventors: Said I. Hakky; A-Hamid Hakki, both of 8547 Merrimoor Blvd., E., Largo, Fla. 34647-3145

[21] Appl. No.: 520,889

[22] Filed: Aug. 31, 1995

[51] Int. Cl.$^6$ .................................................. A61M 29/00
[52] U.S. Cl. .................................................. 604/96; 604/282
[58] Field of Search ........................ 604/96, 282, 280

[56] References Cited

U.S. PATENT DOCUMENTS

| | | | |
|---|---|---|---|
| 4,784,651 | 11/1988 | Hickey | 604/282 |
| 4,796,629 | 1/1989 | Grayzel | 604/96 X |
| 5,195,970 | 3/1993 | Gahara | 604/96 |
| 5,342,301 | 8/1994 | Saab | 604/96 |
| 5,458,572 | 10/1995 | Campbell et al. | 604/96 |

*Primary Examiner*—John D. Yasko
*Attorney, Agent, or Firm*—John Lezdey

[57] ABSTRACT

A collapsible catheter is provided for irrigation or aspiration of the urinary bladder with fluid. The catheter consists of a collapsible hollow elastomeric tube which is open at the proximal end. The distal end portion has at least one stiffened aperture. A plurality of channels are provided along the length of the tube which contain removable wires or rods which stiffen the tube for insertion into the bladder. A balloon means is provided to hold the catheter in place.

13 Claims, 2 Drawing Sheets

COLLAPSIBLE CATHETER

FIELD OF THE INVENTION

The present invention relates to a surgical device and method for draining or feeding a biological system and in particular a collapsible indwelling catheter is provided for draining or aspirating the urinary bladder.

BACKGROUND OF THE INVENTION

A urinary bladder tube is used on patients who are unable to urinate. There are many causes of the inability to urinate. Frequently, surgery or other invasive procedures produce such an effect. Generally, the origin of such a condition differs with age and gender. For example, the inability to urinate in men is commonly caused by a blockage of the urethra passageway by an enlargening prostate. In females, the condition may occur after delivery of a baby. And, in small children, a congenital abnormality obstructing the bladder neck or urethra can produce the condition.

After major surgery, it is advantageous to continuously drain the bladder. Continuous drainage of the bladder is also preferred where medical conditions dictate the necessity of monitoring a patient's urine output. It is well known that close measurement of urine output provides a direct correlation to kidney functions and careful monitoring allows one to identify and prevent kidney failure.

It is important to drain the bladder by an indwelling catheter after prostate or bladder surgery. An indwelling Foley type catheter is usually the catheter of choice. U.S. Pat. No. 5,300,022 to Klapper et al and incorporated herein, shows an improvement over the Foley catheter by providing a second lumen for continuous delivery of a sterile irrigating solution directly into the bladder, and preventing any mixture with the main drainage lumen, thus avoiding any reintroduction of harmful bacteria into the bladder during irrigation.

U.S. Pat. No. 4,701,162 issued to Rosenberg and incorporated herein, shows a Foley catheter with two lumens, one for drainage and one for inflation of the balloon. Having separate lumens for drainage and inflation is common in the prior art. U.S. Pat. No. 5,098,379, which is incorporated herein by reference, discloses a Foley catheter having a balloon portion and a lubricated resilient sleeve. U.S. Pat. No. 5,269,770, which is incorporated herein by reference, shows a dual lumen system and balloon Foley catheter for releasing a bactericidal agent. Similarly, U.S. Pat. No. 5,269,755 which is incorporated therein by reference, shows a Foley urinary catheter with a dual membrane delivery system that allows bactericidal agents to diffuse into the urinary tract.

One thing is clear in the prior art of Foley urinary catheters: none of them teach a collapsible device.

An indwelling catheter drains the bladder and diverts the urine from the wound. Moreover, the bladder can be either continuously irrigated with a three way Foley catheter or hand irrigated at discrete moments when desired. In the three way catheter, one port used is connected to a large fluid reservoir and the other port is used for drainage of the returned fluid. The speed of irrigation can be controlled by different mechanisms or different pumps.

In certain patients the bladder must be drained for many years, as in patients with spinal cord lesions. If the bladder is not drained, the pressure inside it will build up and obstruct the kidneys. Continuous kidney obstruction could end in renal failure and death in only a few weeks. Furthermore, the catheter is used to clear blockages and constrictions of the urinary tract.

Therefore, the use of indwelling catheter is very important and could be life saving.

However, there are many serious draw backs to the stiff indwelling catheter. First, it is painful and certain patients cannot tolerate the catheter. Second, a stiff hollow indwelling catheter invites micro-organisms to invade the bladder and kidneys which may cause a serious infection. Third, for patients who are unable to tolerate the stiff catheter, a hole in the bladder must be created to drain the bladder directly through the anterior abdominal wall. This is a serious procedure and exposes the patient to unnecessary risks of other complications.

Thus, it would be ideal if a Foley catheter was stiff enough to be introduced, but collapsed after insertion. The urethra is naturally in a state of collapse at rest. The present invention will mimic the urethra's physiological status. The pain or discomfort from an indwelling catheter will be reduced. In addition, the incidence of bladder or kidney infection is minimized.

SUMMARY OF THE INVENTION

The present invention relates to a catheter for insertion into a patient which is aimed at reducing the discomfiture experienced with conventional indwelling catheters. The catheter of the invention comprises a substantially collapsible elongated elastomeric tube which is open at a proximal end and has at least one opening at the distal end. A valve means is provided at the proximal end of the tube. The tube is provided with a plurality of horizontal channels containing removable wire or rod means for stiffening the tube when inserting into the patient.

Advantageously, the means for stiffening or collapsing the tube includes a balloon means. The balloon means may be within the tube or along its periphery. Preferably, a small hollow tube connects the balloon to a valve system located near the open proximal end.

In accordance with one embodiment of the present invention, there is provided a device and method for draining and aspirating the urinary system using a collapsible hollow elastomeric catheter tube. In the device, the tube is thin enough to keep it in a state of collapse at rest. The collapsible tube is open at one end, that is, the proximal end, has at least one aperture at the distal end or at the other end, and a rigid tip. The open end has a valve which allows passage of fluid into and out of the tube.

There are one or more holes, at the distal end of the tube, which is the end that connects to the bladder. A circular hollow tube or a thickener portion can be used to reinforce the open end of the catheter tube, which is the end that connects to a calibrated urine bag. The reinforcement prevents collapse of the open end and facilitates the insertion of the tube for connection to a urine bag.

In a three way injection system, an extra hollow tube can be added at the proximal end of the catheter and connected to a reservoir for irrigation. This tube does not need to be reinforced.

A method is also provided for irrigating and aspirating the urinary tract using a device as the present invention describes herein.

OBJECT OF THE INVENTION

Accordingly, it is the general object of this invention to provide a collapsible catheter that mimics the urethra in every respect, thus overcoming the disadvantages of the prior art.

It is a further object of the invention to provide a catheter and method of aspirating the bladder after surgery which can be used with less discomfiture to the patient.

It is a further object of this invention to provide a catheter and method of irrigating the bladder for certain ufological conditions.

It is a further object of this invention to provide a catheter that advantageously can be at least partially stiffened or flaccid when desired, thus minimizing the incidence of infection and reducing the pain or discomfort the patient experiences during the period that the catheter is left indwelling.

It is a further object of this invention to provide a collapsible catheter that advantageously can be stiff or flaccid when desired, thus minimizing the incidence of infection and reducing the pain or discomfort the patient experiences during the period when the tube is left indwelling.

DESCRIPTION OF THE PREFERRED EMBODIMENTS

Figure 1:
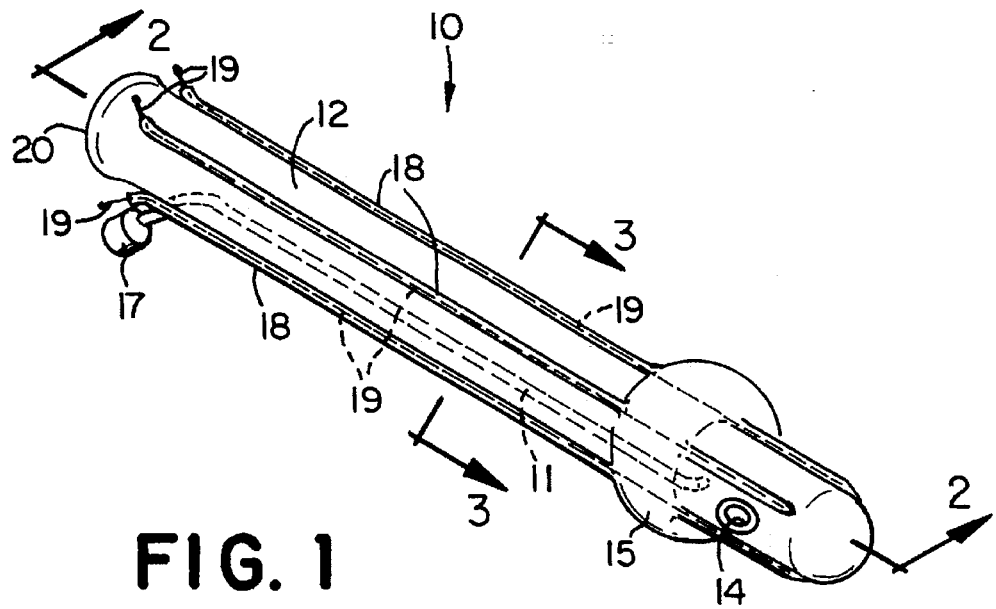
FIG. 1 is a perspective view of the collapsible catheter of the invention.

Although specific terms are used in the following description for the sake of clarity, these terms are intended to refer only to the particular structure of the invention selected for illustration in the drawings and are not intended to define or limit the scope of the invention.

Figure 3:
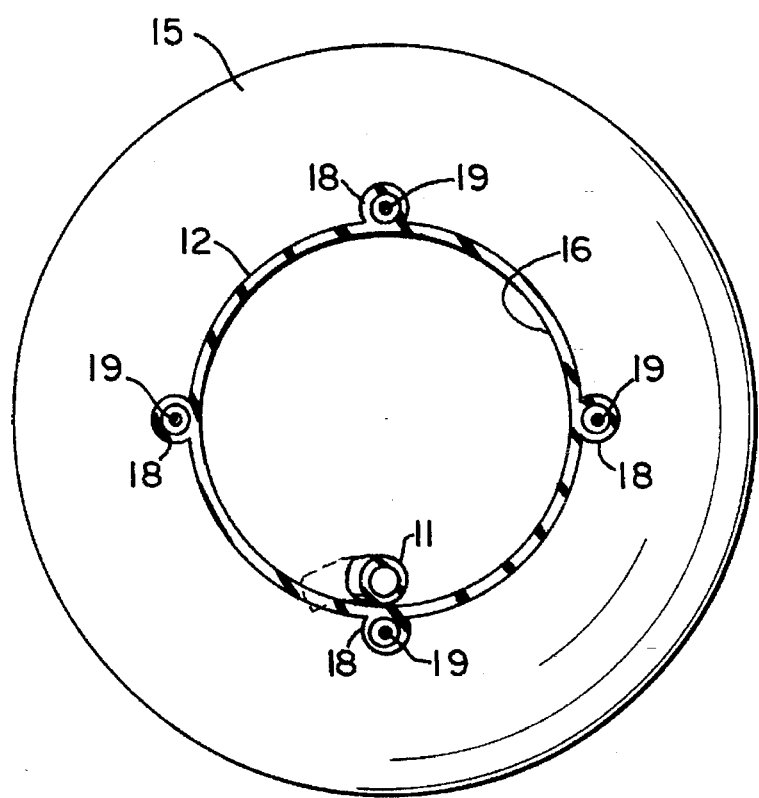
FIG. 3 is a cross-section of the collapsible catheter of FIG. 1 taken along line 3—3.
Figure 2:
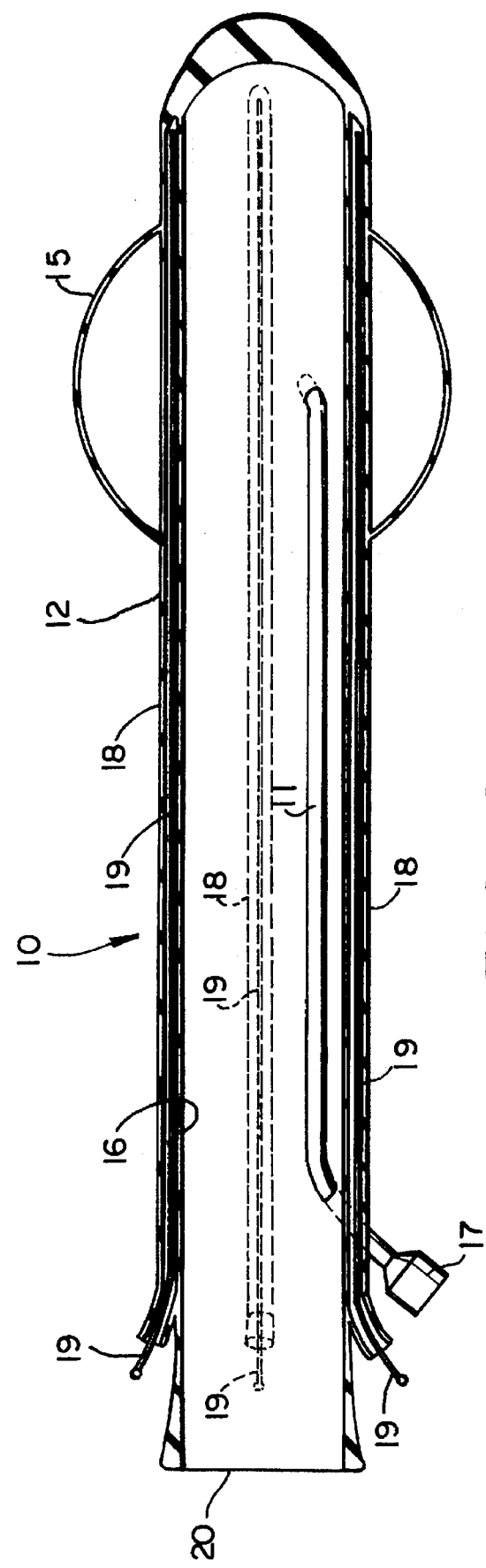
FIG. 2 is a cross-section of the collapsible catheter of FIG. 1 taken along line 2—2.

FIGS. 1–3 show the collapsible catheter of the invention with the removable stiffening means. The collapsible hollow elastomeric catheter 10 comprises a tube 12 which is approximately ten to twenty-five millimeters, preferably about 10 to 15 mm in diameter, thirty to thirty-five centimeters in length, and one tenth of a millimeter in thickness. The tube 12 must be thin enough to keep it in a collapsed state at all times, for example, about a tenth of a millimeter in thickness. There are one or more reinforced openings or holes 14, preferably two or three, located at the distal end of tube 12 which is the end that connects into the bladder. The holes 14 are advantageously six to eight millimeters in diameter. The distal tip is preferably thickened to aid in insertion into the bladder.

The open end 20 of the tube 12 is the end that can be connected to a calibrated urine bag. This end 20 can be thickened or reinforced with a circular hollow tube or a valve to prevent collapse of the open end and facilitate the connection of the tube 12 to a urine bag.

Around the periphery of the tube 12 are a plurality of parallel channels 18 which house removable rods or wires 19 which provide stiffness to the catheter 10 during insertion into the patient. The rods or wires 19 may be metallic, plastic or fiberglass. The channels 18 may be formed within the wall of the tube 12 or on the inner 16 or outer portion of the wall.

To prevent the tube 12 from slipping out of the urinary bladder an inflatable balloon 15 can be provided near the distal end as shown in FIGS. 1 and 3. The balloon 15 may be inflated through the hollow tube or channel 11 which runs along wall 16 to a valve system 17.

In a three way irrigation system an extra hollow tube may be added to the catheter 10. This tube may be connected to a reservoir of fluid for irrigation.

The collapsible tube 12 may be made from silicone rubber, latex rubber or any other suitable medically approved elastomer. The distal end is preferably thickened about 1 to 2 cm so as to provide sufficient stiffness to prevent collapse during drainage. The proximal end preferably has a thickness to prevent collapse of about 2–3 cm in length.

The valve system 17 may be one, two or three ways. The balloon member 15 is attached to the periphery of the catheter 10. The balloon 15 is at least partially inflated to prevent the catheter 10 from slipping out of the urinary bladder. The balloon 15 is attached to the outside of the catheter 10 and is connected to a small hollow tube 11 of the valve system 17 located near the proximal end. The balloon can be filled with air or fluid. When inflated, the balloon can fully or partially support the sides of the tube.

The present invention will mimic the physiological status of the urethra in every respect. In the event of a three way urethral catheter, the fluid will distend the hollow non-reinforced tube when the fluid is turned on. If the fluid is turned off, the infusion or irrigating hollow tube will collapse.

In certain difficult cases, the balloon is then injected with fluid until the catheter is stiff enough to be threaded into the bladder. The balloon of the catheter is then further inflated with fluid to prevent the catheter from slipping out of the bladder. The balloon can then be deflated in the manner just described.

In the method for draining the urinary bladder, the catheter is stiffened by placement of the wires or rods within their channels. The stiffened urethral catheter is well lubricated and passed urethrally into the bladder. Once the urethral catheter is in position, as noted by the return of urine, the balloon at the distal end of the catheter is inflated. After the catheter is secured in the urinary bladder, the fluid in the stiffening wires or rods are withdrawn, which collapses the indwelling catheter.

Although the invention has been described with a certain degree of particularity, it is understood that the present disclosure has been made only by way of example and that numerous changes in the details of construction and the combination and arrangement of parts may be resorted to without departing from the spirit and scope of the invention.

What is claimed:

1. A urinary catheter for insertion into the bladder of a patient, said catheter comprising:
   a) a substantially collapsible elongated elastomeric tube which is sufficiently thin to stay in a state of collapse and is open at a proximal end, the distal end of said tube having at least one opening;
   b) a plurality of channels running substantially along the length of said tube; and,
   c) a removable wire or rod means within said channels for stiffening said tube when inserted into said patient and collapsing said tube when said wire or rod means are withdrawn.

2. The catheter of claim 1 including balloon means for partially collapsing or partially stiffening said tube.

3. The catheter of claim 2 wherein said balloon means is along the periphery of said tube near the distal end.

4. The catheter of claim 1 wherein said channels extend longitudinally substantially along the length of said tube.

5. The catheter of claim 1 wherein said tube comprises latex or silicone rubber.

6. The catheter of claim 7 wherein said tube comprises silicone.

7. The catheter of claim 7 wherein said tube comprises latex.

8. The catheter of claim 1 wherein said catheter is a Foley type catheter.

9. The catheter of claim 1 wherein said opening at the distal end is reinforced to prevent collapse.

10. The catheter claim 9 wherein said opening is approximately six to eight millimeters in diameter.

11. The catheter of claim 1 wherein said tube is reinforced at the proximal end.

12. The catheter of claim 1 wherein said catheter is approximately ten to twenty-five millimeters in diameter, thirty to thirty-five centimeters in length, and a tenth of a millimeter in thickness.

13. A collapsible catheter for insertion into the bladder of a patient comprising:

a) a collapsible hollow elastomeric tube which is closed at one end and open at the other end, said tube being sufficiently thin to stay in a state of collapse and having at least one rigid aperture at the closed end;

b) a plurality of parallel channels substantially along the length of said tube containing removable rods or wires which stiffen said tube when inserted and collapses the tube when withdrawn; and, c) inflatable balloon member attached outside of said tube near said closed end for maintaining the catheter in the bladder.

* * * * *